United States Patent [19]

Ponchiroli

[11] Patent Number: 4,567,163
[45] Date of Patent: Jan. 28, 1986

[54] SALICYCLIC ACID DERIVATIVES OF N-ACETYLCYSTEINE AND PHARMACOLOGICAL USE THEREOF

[75] Inventor: Osvaldo Ponchiroli, Milan, Italy

[73] Assignee: Pietro Ismardi & C. Spa, Oneglia, Italy

[21] Appl. No.: 442,044

[22] Filed: Nov. 16, 1982

[30] Foreign Application Priority Data

Nov. 20, 1981 [IT] Italy ..................................... 25198 A

[51] Int. Cl.⁴ ................... A61K 31/265; A61K 31/71; A61K 31/65; C07C 153/023
[52] U.S. Cl. ................................. 514/29; 260/455 R; 260/351.1; 514/513; 514/36; 514/152; 536/7.4; 536/13.2
[58] Field of Search .......................... 260/455 R, 351.1; 514/513, 36, 152, 29; 536/7.4, 13.2

[56] References Cited

U.S. PATENT DOCUMENTS 4,268,456  5/1981  Keim et al. ..................... 260/455 R

OTHER PUBLICATIONS

CA: 88:23,388p., Blum.
El-Naggar et al., CA: 83:43714s.

*Primary Examiner*—Henry R. Jiles
*Assistant Examiner*—Robert C. Whittenbaugh
*Attorney, Agent, or Firm*—Martin Smolowitz

[57] ABSTRACT

The thioester of N-acetylcysteine with salicylic acid and the pharmacologically acceptable and non-toxic organic and inorganic salts thereof, exhibit anti-pyretic, anti-inflammatory and analgesic activity as well as mucolytic activity. The compounds are prepared by the reaction of N-acetylcysteine with either the acid chloride of acetylsalicylic acid or with the mixed anhydride formed from acetylsalicylic acid and ethyl chloroformate, the reaction taking place in an aqueous medium and at low temperature.

9 Claims, No Drawings

SALICYCLIC ACID DERIVATIVES OF N-ACETYLCYSTEINE AND PHARMACOLOGICAL USE THEREOF

The present invention relates to the thioester of N-acetylcysteine with salicylic acid and the pharmaceutically acceptable and non toxic organic and inorganic salts thereof, of the formula:

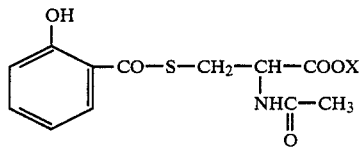

wherein X is hydrogen, an alkali metal, an alkaline earth metal, or the radical of an organic base, particularly a basic amino acid or a basic antibiotic.

It has been discovered, and confirmed by preliminary tests on the pharmacological activities, that there not only are maintained the specific properties of acetylsalicylic acid and of N-acetylcysteine, i.e. the anti-pyretic, anti-inflammatory and analgesic activities of the former and the mucolytic activity of the latter, but these properties are also surprisingly improved in the compounds of this invention, the latter being thus suitable for use as expectorant, mucolytic, anti-pyretic and anti-inflammatory drugs.

As stated above the present invention also relates to the pharmaceutically acceptable, non-toxic, organic and inorganic salts of the thioester of N-acetylcysteine with salicylic acid.

Among the inorganic bases which are useful for this purpose, those of alkali and alkaline earth metals are contempleted, whereas among the organic bases, basic amino acids, such as arginine and lysine, and basic antibiotics, such as erythromycin, propionylerythromycin, neomycin, mechlocycline and so on are of particular importance, the specific properties and activities of the bases being thus exploited.

The method also being an object of the present invention essentially comprises the following steps:
(a) preparing the chloride of acetylsalicylic acid by means of a chlorinating agent known per se, or preparing the mixed anhydride of acetylsalicylic acid and ethyl chloroformate;
(b) reacting N-actylcysteine, at a low temperature in an aqueous ester medium and in the presence of an organic or inorganic base acting as acid acceptor with the chloride of acetylsalicylic acid or the mixed anhydride of acetylsalicylic acid and ethyl chloroformate;
(c) isolating pure deacetylated ester and possibly converting the same into the corresponding organic or inorganic salts in an aqueous, alcoholic or ketonic medium.

According to the preferred embodiment of the invention the chlorination of acetylsalicylic acid is carried out by means of thionyl chloride, the reaction mass is refluxed, and the esterification is carried out in water and at a temperature ranging from 1° C. to 5° C.

Included among the ester solvents suitable for the reaction of the above mentioned process are, for example, ethyl acetate, isopropyl acetate, and so on.

An alkali metal hydroxide or a tertiary amine, such as, for example, triethylamine, can be used as an organic or inorganic base having acid acceptor activity.

As regards step (c), it should pointed out that the reaction mixture will consist partly of an already deacetylated product and partly of a still acetylated ester. In such a case, before isolation is carried out, the deacetylation of the acetylated portion is carried out, for example, by reaction with an organic base.

It is finally to be noted that in the process of the invention, by N-acetylcysteine there is meant the levorotatory form thereof, i.e. the usually available one. This meaning should not in any case be intended as an improper limitation of the invention.

Additionally the reaction temperature of step (3) does not exceed 5° C.

The invention will be now illustrated by the following non-limiting examples.

EXAMPLE 1

(a) Chlorination of acetylsalicylic acid 100 g of acetylsalicylic acid are placed into a 3-necked flask equipped with a stirrer, a smoke trap, and a reflux condenser, together with 25 mls of anhydrous chloroform and 250 mls of thionyl chloride. The mass is slowly heated under stirring and after about 40 minutes of refluxing a perfect solution having a pale yellow color is obtained.

After the evolution of gaseous $SO_2$ and HCl has been completed, the reaction mixture is cooled under stirring to room temperature, and then concentrated under vacuum to eliminate the excess solvent and thionyl chloride, thus obtaining a straw-coloured liquid (110.3 g).

(b) Mixed anhydride of acetylsalicylic acid and ethyl chloroformate 18 g of acetylsalicylic acid are charged into a 3-necked flask, equipped with a stirrer and with a separatory funnel, together with 180 mls of anhydrous benzene and 11 g of ethyl chloroformate.

The mass under stirring is cooled to a temperature of about 0° C., then 10 g of triethylamine are slowly added, thus giving place to a heterogeneous reaction mass containing a precipitate which is filtered under vacuum, and a solution of the anhydride is obtained which, when concentrated, gives 25 g of a yellow limpid oil.

(c) Preparation of salicyloylthio-N-acetylcysteine

A 1 l flask, equipped with a stirrer and with an outer refrigerating bath, is charged with 102.8 g of the sodium salt of N-acetylcysteine and 700 mls of water.

The solution is cooled to a temperature of between 1° and 5° C., and a solution of 22.2 g of NaOH, dissolved in 120 mls of water, and of acetylsalicyloylchloride is slowly added.

The addition is adjusted so that the temperature does not exceed 5° C. and it is completed within about 1 h.

After the addition has been terminated, the temperature of the reaction mixture, the latter being maintained under stirring, increases spontaneously to 15° C.; then the reaction mixture is allowed to stand still under stirring, for about 1 h.

The reaction mixture is slowly acidified and the finished product is extracted with 700 mls of methyl isobutyl ketone.

The ketonic phase is separated, washed with water, dried, filtered over charcoal, and concentrated. There are obtained 180 g of dense oil, comprising both the desired ester and a not negligible amount of acetylated compound, i.e. the acetylsalicylic ester.

32.5 g of this product are reacted with 0.1 mole of an organic base, such as DL-lysine, freshly, obtained as a 50% aqueous solution, in admixture with methanol and isopropanol. The thus obtained salt (with a yield of 75% of the theoretical value) is in the form of white crystals having a m.p. of 110°–112° C.

20 g of this product are dissolved in 100 mls of distilled water and acidified with 0.5 N hydrogen chloride up to pH 3.5 under stirring.

The salicyloylthio N-acetylcysteine is obtained as white crystals which after filtration, washing and drying amount to a yield of 10 g with a m.p. of 173°–175° C.

1 g of crude salicyloylthio N-acetylcysteine can be crystallized with 10 mls of a water/ethanol (50/50) solution thus obtaining an 80% yield of a chromatographically pure product having a m.p. of 192°–195° C.

The product, which has the formula (1), in which $X=H$, and a molecular weight of 283.31, appears as a non-hygroscopic white colored microcrystalline powder, slightly soluble in cold water, partly soluble in alcohols and insoluble in chloroform and in ethers. From the chromatographic analysis on silica gel using ethyl acetate/ethanol/acetic acid (35:20:2) as eluant, U.V. light as detector and a $FeCl_3$ 8% solution, an Rf value of 0.54 is found.

EXAMPLE 2

Sodium salt of salicyloylthio-N-acetylcysteine

To a suspension of 1 mole of salicyloylthio-N-acetylcysteine in an equilibrium mixture of dioxane and water the stoichiometric amount of $NaHCO_3$ is added, the reaction temperature being maintained at a value not higher than $+10°$ C. The thus obtained solution is lyophilized to give the pure crystalline form of the sodium salt.

EXAMPLE 3

Erythromycin salt of salicyloylthio-N-acetylcysteine

Erythromycin base (13 g) is reacted with 5 g of salicyloylthio-N-acetylcysteine in 10 mls of ethyl acetate.

A homogeneous phase is obtained, then 4 mls of water are added and a white crystalline product is formed which after 48h is filtered, washed and dried, whereby the desired salt is obtained with a yield of 67% (of the theoretical value), having a m.p. of 83°–87° C.

EXAMPLE 4

Erythromycin monopropionate salt of salicyloylthio-N-acetylcysteine

Erythromycin monopropionate (14 g) is reacted with 5 g of salicyloylthio-N-acetylcysteine in 100 mls of anhydrous cyclohexane.

There is thus obtained a suspension, which is stirred and slowly mixed with 6 mls of methanol and a transformation of the crystalline characteristics takes place.

The stirring is continued during 2h; then filtration, washing and drying are carried out. The salt is obtained with a yield of 95% of the theoretical value in the form of a white powder with a transformation point at 100° C.

EXAMPLE 5

0.1 mole of mechlocycline base is stirred with a mixture of water (30 mls) and ethanol (30 mls) and then 0.1 mole of salicyloyl-N-acetylcysteine are added. A homogeneous phase is obtained.

After the solution becomes completely homogeneous, isopropylic acid (20 mls) is slowly added.

A yellow product precipitates.

After filtration 5.6 g of salt are obtained having a m.p. of 85°–90° C. (with decomposition).

The derivatives of the invention have been subjected to toxicological and pharmacological tests, and hereinafter only the data relating to the lysinate of salicyloylthio-N-cysteine are reported without any intended limitation. There were found in the mouse the following $LD_{50}$ values:

$LD_{50}$ (oral) 4000 mg/kg $LD_{50}$ (intraperitoneal route) 3000 mg/kg

In the rat the following $LD_{50}$ values were found:

$LD_{50}$ (oral) 4000 mg/kg $LD_{50}$ (intraperitoneal route) 1460±235 mg/kg.

In the carrageenin induced oedema test, an $ED_{33}$ value of 235 mg/kg was detected. In the arthritis test induced by Freund adjuvant, there was found an $ED_{33}$ value of 131 mg/kg.

In the test on the analgesic activity inhibition test of stretching or writhing induced by acetic acid an $ED=210$ mg/kg was found.

In the test of mucolytic activity in vitro, the viscosity of mucus was reduced by about 8% by a concentration of the tested compound of 0.05 mole.

In the test of antipyretic activity an $ED_{75}$ value of 427 mg/kg was found.

The derivatives of the present invention are used to prepare pharmaceutical compositions suitable for the desired administration route, together with the usual carriers, excipients and fillers and by means of the usual pharmaceutical manufacturing technologies, the foreseen therapeutic dosages being between 0.3 and 1 g.

As regards the specific case of the salt with mechlocycline, the dermatological activity of which is known, the therapeutic activity of the antibiotic becomes improved and completed.

I claim:

1. A compound of the formula:

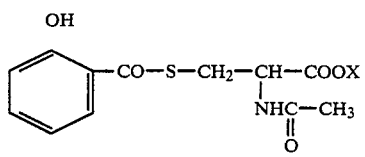

wherein X is selected from the group consisting of hydrogen, alkali metals, alkaline earth metals, and the radicals of organic bases.

2. The compound according to claim 1, wherein said organic base is a basic amino acid.

3. The compound according to claim 2, wherein said basic amino acid is selected from the group consisting of lysine and arginine.

4. The compound according to claim 1, wherein said organic base is a basic antibiotic.

5. The compound according to claim 4, wherein said basic antibiotic is selected from the group consisting of erythromycin, propionylerythromycin, neomycin and mechlocycline.

6. The compound according to claim 1, wherein said alkali metal is sodium.

7. A pharmaceutical composition having anti-pyretic, anti-inflammatory, analgesic and mucolytic activity, comprising an effective amount for said activity of the compound of claim 1.

8. The pharmaceutical composition according to claim 7, in suitable form for oral, parenteral, rectal and topical administration.

9. A pharmaceutical composition in suitable form for topical administration, having dermatological activity, comprising a dermatologically effective amount of the mechlocycline salt of the compound according to claim 1.

* * * * *